(12) United States Patent
Trutwig et al.

(10) Patent No.: US 11,589,450 B2
(45) Date of Patent: Feb. 21, 2023

(54) FLAT FLEXIBLE COATING ARRANGEMENT

(71) Applicant: CINOGY GMBH, Duderstadt (DE)

(72) Inventors: Leonhard Trutwig, Duderstadt (DE);
Mirko Hahnl, Berlingerode (DE);
Karl-Otto Storck, Duderstadt (DE);
Melanie Ricke, Katlenburg-Lindau (DE); Dirk Wandke, Heilbad Heiligenstadt (DE); Dirk Simon, Bovenden (DE)

(73) Assignee: CINOGY GMBH, Duderstadt (DE)

( * ) Notice: Subject to any disclaimer, the term of this patent is extended or adjusted under 35 U.S.C. 154(b) by 683 days.

(21) Appl. No.: 16/497,884

(22) PCT Filed: May 31, 2017

(86) PCT No.: PCT/DE2017/100461
§ 371 (c)(1),
(2) Date: Sep. 26, 2019

(87) PCT Pub. No.: WO2018/177448
PCT Pub. Date: Oct. 4, 2018

(65) Prior Publication Data
US 2020/0029414 A1    Jan. 23, 2020

(30) Foreign Application Priority Data
Mar. 28, 2017   (DE) .................... 10 2017 106 570.9

(51) Int. Cl.
*H05H 1/24*         (2006.01)
*A61B 18/04*        (2006.01)

(52) U.S. Cl.
CPC ......... *H05H 1/2406* (2013.01); *A61B 18/042* (2013.01); *H05H 1/2418* (2021.05);
(Continued)

(58) Field of Classification Search
None
See application file for complete search history.

(56) References Cited

U.S. PATENT DOCUMENTS 9,005,188 B2 *  4/2015  Wandke ............... A61N 1/0476
                                                  606/32
9,330,890 B2 *  5/2016  Busse .................. H05H 1/2406
(Continued)

FOREIGN PATENT DOCUMENTS

WO    2009067682 A2   5/2009
WO    2012150041 A1   11/2012
(Continued)

OTHER PUBLICATIONS

K Heuer et al The topical use of non-thermal dielectric barrier discharge (DBD): Nitric oxide related effects on human skin vol. 44, Jan. 30, 2015 Nitric oxide.*

*Primary Examiner* — Srinivas Sathiraju
(74) *Attorney, Agent, or Firm* — WCF IP

(57) ABSTRACT

The invention relates to a flat flexible coating arrangement comprising a coating surface (9) for placing on a body region of a living being and at least one electrode (3, 3') arranged above the coating surface (9), and a dielectric (1) containing the at least one electrode (3, 3'), the at least one electrode (3, 3') comprising a supply line for an AC high voltage in order to form a dielectrically impeded plasma. Said arrangement enables fusion processes over the course of the plasma treatment and optionally wound healing without removing the coating arrangement from the body region by means of at least one built-in sensor (14) for determining at least one parameter of the body region.

9 Claims, 2 Drawing Sheets

Figure 1:
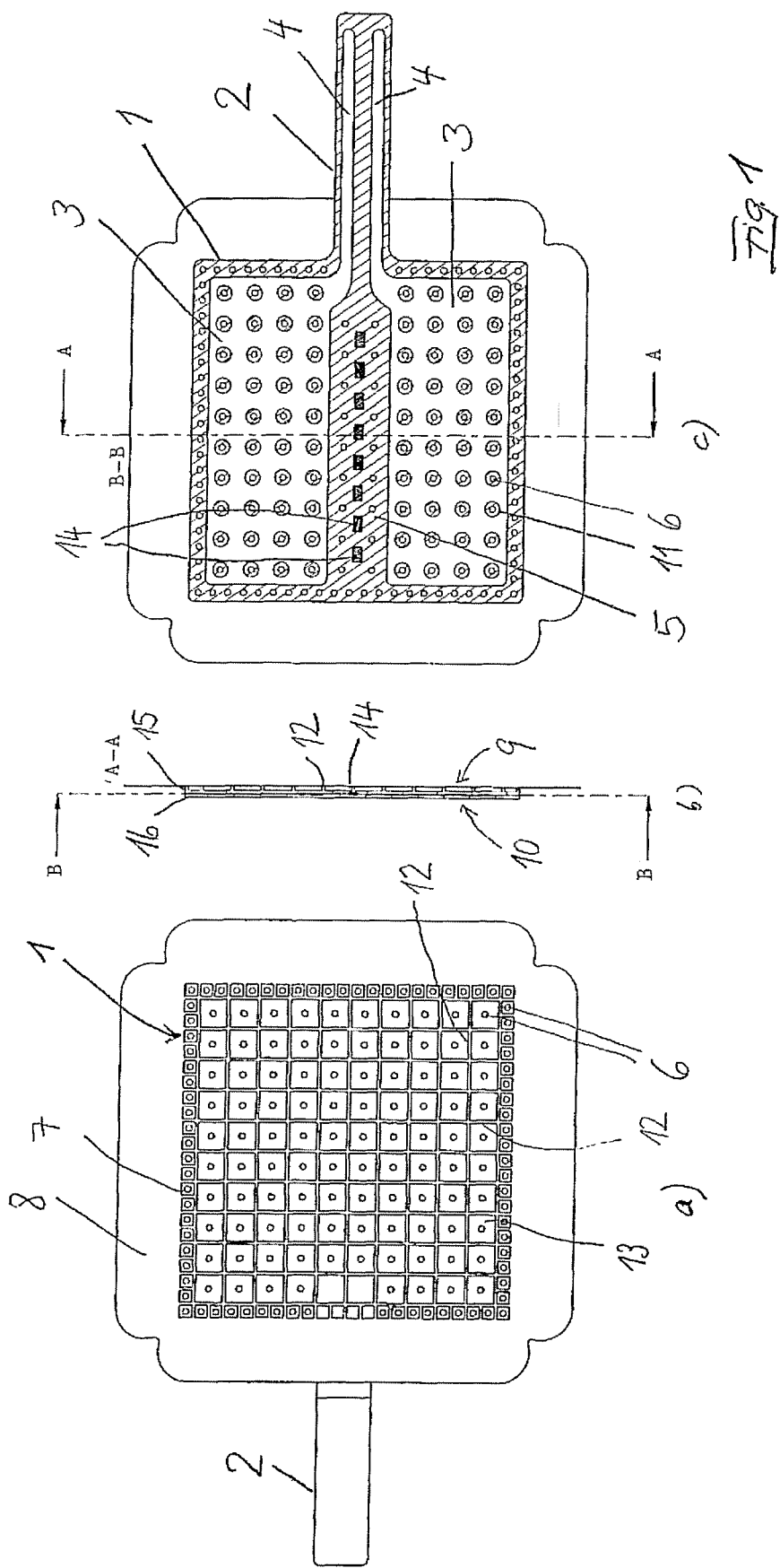

(52) U.S. Cl.
CPC ..... *H05H 2240/10* (2013.01); *H05H 2240/20* (2013.01); *H05H 2245/30* (2021.05); *H05H 2245/40* (2021.05); *H05H 2277/14* (2013.01)

(56) References Cited

U.S. PATENT DOCUMENTS

| | | | | |
|---|---|---|---|---|
| 9,889,218 | B2* | 2/2018 | Morfill | H05H 1/2406 |
| 10,265,116 | B2* | 4/2019 | Stieber | A61B 18/042 |
| 10,391,327 | B2* | 8/2019 | Skiera | A61L 2/0011 |
| 10,786,593 | B2* | 9/2020 | Deane | F24F 8/192 |
| 11,006,995 | B2* | 5/2021 | Stieber | A61B 18/042 |
| 11,224,755 | B2* | 1/2022 | Skiera | H05H 1/2406 |
| 2012/0046597 | A1* | 2/2012 | Morfill | H05H 1/2406 604/20 |
| 2012/0259270 | A1* | 10/2012 | Wandke | A61N 1/0476 604/23 |
| 2013/0345620 | A1 | 12/2013 | Zemel et al. | |
| 2014/0182879 | A1* | 7/2014 | Busse | A61N 1/40 29/874 |
| 2015/0202452 | A1* | 7/2015 | Skiera | A61L 2/14 604/23 |
| 2017/0094769 | A1* | 3/2017 | Eckert | A61B 18/042 |
| 2017/0231680 | A1* | 8/2017 | Mahrenholz | A61B 18/10 606/34 |
| 2017/0232132 | A1* | 8/2017 | Deane | F24F 8/192 422/121 |
| 2019/0076225 | A1* | 3/2019 | Morfill | A61L 2/18 |
| 2019/0183559 | A1* | 6/2019 | Stieber | H05H 1/2439 |
| 2019/0336781 | A1* | 11/2019 | Skiera | A61L 2/0011 |
| 2020/0029414 | A1* | 1/2020 | Trutwig | H05H 1/2406 |
| 2020/0069956 | A1* | 3/2020 | de Penning | A61B 18/042 |
| 2021/0033293 | A1* | 2/2021 | Soberon | A61L 9/22 |
| 2022/0047880 | A1* | 2/2022 | Planard-Luong | H05H 1/2406 |

FOREIGN PATENT DOCUMENTS

| | | | | |
|---|---|---|---|---|
| WO | | 2013/040542 A1 | 3/2013 | |
| WO | | 2016/037599 A1 | 3/2016 | |
| WO | WO-2018093261 A1 * | | 5/2018 | ........... A61B 18/042 |

* cited by examiner

FLAT FLEXIBLE COATING ARRANGEMENT

The invention relates to a planar flexible contact arrangement having a contact surface formed for contact on a in the body region of a living being and at least one electrode arranged above the contact surface and a dielectric material embedding the at least one electrode, wherein the at least one electrode comprises a supply line for an AC high voltage to form a dielectric barrier plasma.

Such a planar flexible contact arrangement is known as a wound contact arrangement from WO 2016/037599 A1. The dielectric barrier plasma formed at the wound has a germicidal effect and ensures improved wound healing, since infections of the wound can be precluded if the plasma is generated at sufficient intervals for a certain time. Designing the corresponding wound contact arrangement in such a way that wound secretion is suctioned off and a certain partial vacuum effect is also exerted if needed on the wound is known.

In addition, a fluid assisting the wound healing can be brought into the region of the wound through passage openings in the wound contact arrangement, which project through the dielectric material but are accompanied by secure insulation in relation to the at least one electrode.

The combination of the conventional wound healing measures with the germ reduction in the region of the wound by way of a repeatedly exerted plasma treatment, which is possible without removing the wound contact arrangement from the wound, has proven itself in practice.

Furthermore, also subjecting an intact skin surface of a body region to a plasma treatment in order to improve the structure of the skin surface and possibly to promote the micro-circulation in the skin is known.

The present invention is based on the object of further improving the contact arrangement to enable an improved and controlled plasma treatment of the body region.

To achieve this object, the planar flexible contact arrangement of the type mentioned at the outset is characterized according to the invention by at least one integrated sensor for ascertaining at least one parameter of the body region.

The contact arrangement thus contains at least one sensor, using which the body region can be monitored. It is possible in this case that a sensor is used which reacts physically or chemically and in this case causes a readable display in the form of an optical change (color, transparency, etc.). For example, the pH value may be checked by a sensor like a reagent paper (for example, litmus paper) and displayed by a color change. However, it is also possible and reasonable for the display of various parameters if at least one integrated sensor is connected to an electric voltage, by which its function or the analysis of the sensor signal is enabled. This has the advantage that a warning or a control, for example of the plasma treatment, is automatically possible as a function of the measured parameter.

With respect to the type of the sensors, it is possible, for example, to measure the perfusion in the body region using miniature sensors integrated into the contact arrangement, for example by measuring the oxygen saturation. Such sensors, which operate at wavelengths in the visible and infrared range, are known and therefore do not have to be explained in greater detail here.

It is furthermore possible to measure the temperature distribution in the body region and in particular to establish the rise of a temperature by way of temperature sensors in the contact arrangement. The temperature increase can be an indicator of an inflammation which is occurring or has occurred, in particular in a wound. In a similar manner, a color change in the body region can be detected using optical measuring methods. It can be established, for example, by corresponding light-emitting diodes and phototransistors, which react to a specific color spectrum, whether the reddening of a wound recedes in the healing process or strengthens again due to an infection.

Of course, it is possible to house in the contact arrangement multiple sensors, which can measure the same parameter or also various parameters. In this manner, automatic wound monitoring is possible without the contact arrangement, using which the healing process is accelerated because of the plasma treatment, having to be removed from the wound, whereby already healed tissue will possibly be torn open again and a risk of infection will be induced.

In a further embodiment, it is possible that the sensor ascertains the pH value in the body region.

The ascertainment of the measured values by the at least one sensor is advantageous in particular if the treated body region represents a wound. The wound healing may be promoted by the plasma treatment and if necessary repeated again and again at suitable intervals in a manner controlled by the measured values, without the contact arrangement having to be removed from the wound. However, the contact arrangement is also suitable for the treatment of body regions which are not in the form of a wound. Even in the case of an intact skin surface, for example, the treatment of a micro-circulation breakdown, and thus an oxygen undersupply, or, for example, a skin infection can be reasonable. The at least one sensor can also give important indications during the treatment for an intact skin surface which has not developed into a wound, for example by measuring the oxygen saturation, the temperature, skin reddening, and/or a pH value.

The measured values acquired by the at least one sensor can be transmitted via a connected cable or also via wireless data transmission, for example according to the Bluetooth standard, and can be immediately analyzed or buffered. The buffering can also take place if needed in a memory chip in the contact arrangement, so that the measured values can be read out during a regular inspection of the body region. Alternatively, it is possible to provide the contact arrangement with a warning signal generator, which emits a warning signal if set threshold values are exceeded.

The at least one sensor can also be used to control the plasma treatment while the contact arrangement is applied to the affected body region. For example, in the event of an established low oxygen saturation, the plasma discharge can be started to positively influence the healing or treatment process.

The voltage supply for the at least one sensor can take place via a separate cable, via which the at least one electrode of the contact arrangement is supplied with a high voltage. It is conceivable to derive the voltage supply for the at least one sensor and the microprocessor activating and possibly analyzing it from the high voltage for the plasma treatment. However, the voltage supply would then only be available during the plasma treatment. The measured values could then only be acquired during the plasma treatment. It is therefore expedient either to transmit the voltage supply via a separate supply cable to the at least one sensor and its control circuit in the contact arrangement or to integrate into the contact arrangement a micro-battery, which provides the energy required for the operation of the sensors and the control circuit. It is also conceivable to also take the treatment energy required for the duration of the treatment for carrying out the plasma treatment from integrated batteries, wherein then there is additionally integrated the contact arrangement a high-voltage step, which generates the required pulsed AC high voltage for the plasma generation from the low battery voltage and conducts it to the at least one electrode.

It is furthermore conceivable to integrate into the contact arrangement for the sensors a small accumulator, which is charged with externally supplied energy during the plasma treatment, by a small fraction of the supplied energy being branched off for the charging of the accumulator.

For the contact arrangement according to the invention, it is possible to use a single electrode for generating the plasma and to use the skin or the body, respectively, of the wound region to be treated as a counter electrode (ground). In this way, an advantageous treatment depth is achieved in the region of the wound.

It is furthermore possible to provide at least two electrodes in the contact arrangement, which are supplied with the AC high voltage in counter phase, wherein the body of the skin surface to be treated again functions as a counter electrode.

In a further embodiment, at least two electrodes can be provided, between which the high-voltage alternating field is generated, so that the plasma results between the electrodes and can become active as a surface plasma in the body region. In this way, however, with a normal introduction of energy, only low treatment depths in the body region are possible.

The invention is to be explained in greater detail hereafter on the basis of exemplary embodiments schematically illustrated in the drawing, in which:

FIG. 1a) shows a view of a contact side of a first embodiment of a contact arrangement;

FIG. 1b) shows a vertical section along line A-A in FIG. 1c);

FIG. 1c) shows a horizontal section along line B-B in FIG. 1b);

FIG. 2a) shows a view of a contact side of a second embodiment of a contact arrangement;

FIG. 2b) shows a vertical section along line A-A in FIG. 2c);

FIG. 2c) shows a horizontal section along line B-B in FIG. 2b);

FIG. 2d) shows a separate illustration of the electrodes having electronic components, supply batteries, and connecting lines of the second embodiment.

The exemplary embodiment illustrated in FIG. 1 shows a substantially rectangular contact arrangement having a planar rectangular dielectric material 1, which extends on one side into a web-shaped attachment 2. Two planar electrodes 3 are embedded adjacent to one another in the dielectric material 1, the areas of which inside the dielectric material 1 are shown shaded in FIG. 1. The electrodes 3 thus do not extend up to the edge of the dielectric material 1, since they are also to be enclosed by the dielectric material 1 at the edge and are therefore to be completely insulated to the outside. The electrodes 3 each extend with a planar conductor track 4 into the web-shaped attachment 2, so that the electrodes 3 can be supplied with the AC high voltage required for plasma generation at the web-shaped attachment 2. This takes place with contacting technology known per se, preferably with the aid of cutting contacts of a contact element connected to a high-voltage line. The cutting contacts can cut into the dielectric material of the web-shaped attachment 2 and thus establish the contact with the conductor tracks 4 of the electrodes 3.

Along a longitudinal axis of the web-shaped attachment 2, the electrodes 3 are separated from one another in the dielectric material 2 by a spacing 5, so that the spacing forms a middle strip in the dielectric material in which no electrodes 3 are located.

As may be seen from FIG. 1, the dielectric material comprises regularly arranged passage holes 6, which are also located in a peripheral edge 7 of the dielectric material 1 which is free of the electrodes 3. A peripheral strip 8, which is formed so as to be particularly flexible, having a low thickness, and so as to be adhesive on its lower side, adjoins the edge 7 of the dielectric material 1 in order to enable the fastening of the wound contact arrangement on the skin, possibly around a wound.

The passage holes 6 of the dielectric material also extend through the electrodes 3, so that they extend through the dielectric material 1 from a lower contact surface 9 up to an upper side 10. For example, wound secretion can be suctioned off through the passage openings 6 if the contact arrangement has a partial vacuum source applied to it on the upper side 10 and is covered in a sealed-off manner.

Respective corresponding passage holes 11 of the electrodes 3 align with the passage holes 6 of the dielectric material. These passage holes 11 have a larger diameter than the passage holes 6, so that the edge of the passage holes 11 of the electrodes 3 is covered by dielectric material if the passage holes 6 of the dielectric material 1 form a smooth continuous channel having a constant cross section.

The contact surface 9 of the dielectric material is provided below the electrodes 3 with intersecting webs 12 forming a grid, which delimit square chambers 13, which are open toward the contact surface 9 in the illustrated exemplary embodiment, within the dielectric material 2. The chambers 13 represent air chambers, in which the plasma forms below the electrodes 3 when the electrodes 3 are provided with a suitable high voltage. The electrodes 3 are furthermore covered in this case toward the chambers 13 by a layer of the dielectric material 1. The passage holes 6 of the dielectric material are located centrally in the chambers 13.

The free edges of the webs 12 thus jointly form the contact surface 9 for the contact arrangement.

In the illustrated exemplary embodiment, eight sensors 14 are arranged at equal spacing in relation to one another in extension of the longitudinal axis of the web-shaped attachment 2 in the spacing 5 between the electrodes 3. The sensors 14 are embedded in the dielectric material 1.

As FIG. 1b) indicates, in the illustrated exemplary embodiment, the dielectric material 1 is produced from two layers 15, 16. Firstly, the lower layer 15 is formed having the chambers 12 delimited by the webs 13, wherein the upper side of the lower layer 15 represents a continuous insulating surface. The sensors 14 and the electrodes 3 are applied to the lower layer 15, so that the sensors 14 and the electrodes 3 are completely embedded by the application of the upper layer 16. The material of the electrodes 3 can be in this case by metallic foils, but also by a layer of a plastic material having conductive additives, wherein the plastic material can be the material of the dielectric material. The connection of the two layers 15, 16 of the dielectric material 1 is suitably carried out thermally, by the lower layer 15 being superficially melted somewhat during the application of the upper layer, whereby a materially-bonded connection results. Alternatively, the dielectric material 1 can also be produced in one piece in a single injection-molding procedure if the electrodes 3 and the sensors 14 are inserted into the mold.

If the sensors 14 are to be supplied with a separate supply voltage via the web-shaped attachment 2, a corresponding conductor track can be laid in the web-shaped attachment and the contacting can take place therein.

The sensors 14 can be designed as optical sensors, so that they do not require direct contact with the skin of the patient. However, it is recognizably also possible to form the dielectric material below the sensors without chambers 12 and to terminate the sensors flush with the contact surface 9. In this case, the sensors 14 are already embedded during the production of the lower layer 15 of the dielectric material 1.

Figure 2:
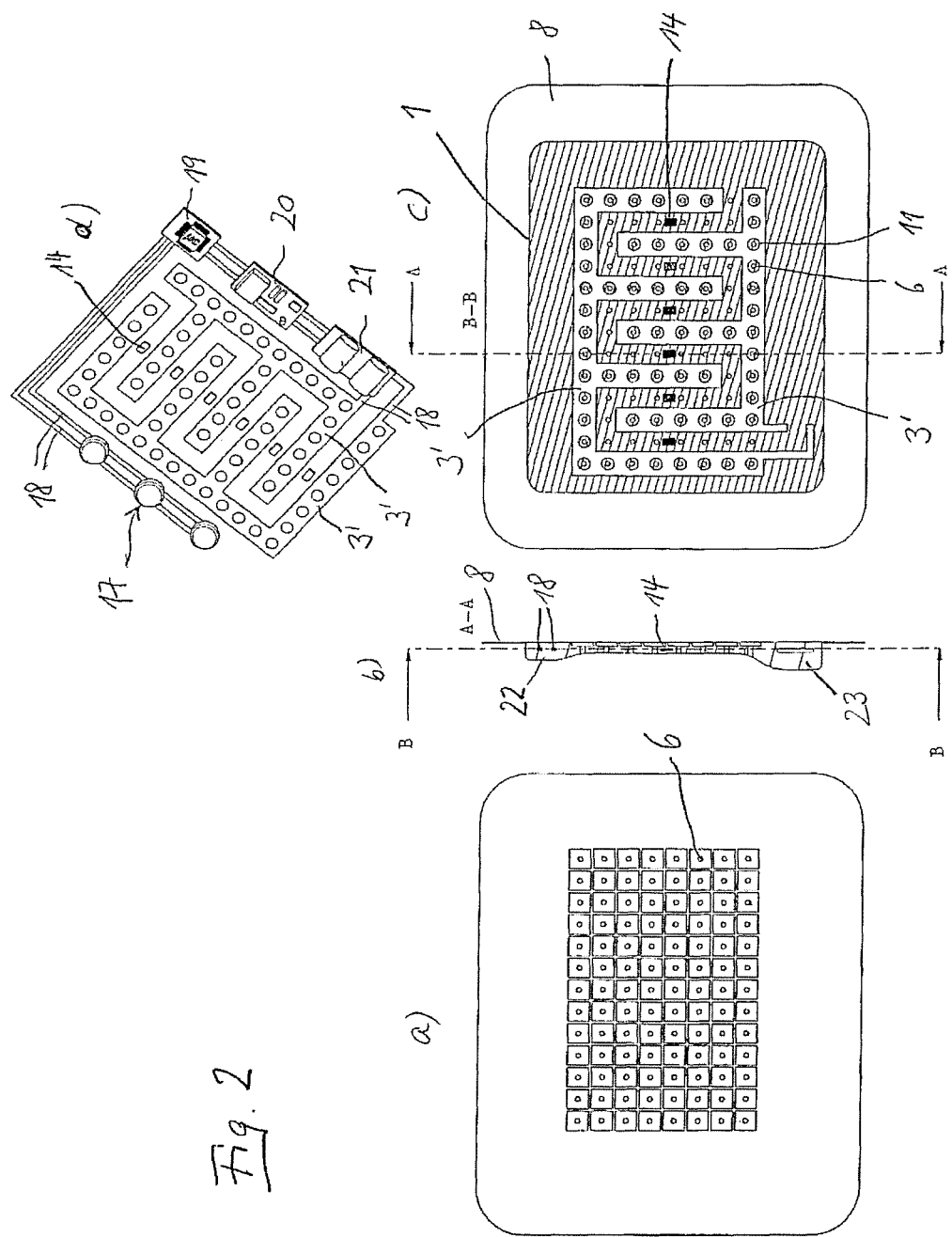

The embodiment shown in FIG. 2 corresponds in substantial parts to the embodiment in FIG. 1, so that parts corresponding to one another are provided with identical reference signs. A dielectric material 1 is also enclosed by a strip 8 used for fastening on the skin in this embodiment. Two electrodes 3' are also provided, which are not arranged adjacent to one another as coherent electrode surfaces here, however, but rather are formed comb-shaped, wherein the tines of the two comb-shaped electrodes 3' are interlaced antiparallel with one another. A spacing 5' thus results between the electrodes 3', which extends in meandering form.

In this exemplary embodiment, the dielectric material 1 is provided with passage holes 6 in the region of the electrodes 3'. The electrodes 3' have larger passage holes 11 where the passage holes 6 extend through electrodes 3'.

The sensors 14 are arranged here on a center line in portions of the meandering spacing 5 extending parallel to one another.

The special feature of this contact arrangement is that it does not require an external voltage supply, but rather comprises integrated in the dielectric material a battery arrangement 17 made of three micro-batteries, from which two conductor tracks 18 lead to a microcomputer 19, at the output of which a controller 20 and, adjoining it, a high-voltage step 21 having two transformer coils are connected. At the output of the high-voltage step 21, the two electrodes 3' are connected via conductor tracks 18.

It is readily recognizable that the sensors are connectable in a routine manner (not shown) to the microcomputer 19, using which the data measured by the sensors 14 can be stored or analyzed and possibly displayed.

FIG. 2*b*) illustrates that, for the battery arrangement 17 and also for the arrangement of microcomputer 19, controller 20, and high-voltage step 21, the dielectric material is formed having thickened areas 22, 23 to be able to accommodate the corresponding components inside the dielectric material 1. A suitable interface can be attached to the thickened area 23 in which the microcomputer 19 is also located to be able to read data out of the microcomputer 19. Of course, it is also possible to make the data wirelessly retrievable.

The sensors (14) or at least one of them can also manage without voltage supply if they physically or chemically react to physical parameters to be monitored and thus generate an optical or possibly electrical signal. The optical signal can consist of a visible change of the material as a function of the environmental parameter, as is known from indicator papers for the pH value, for temperatures, etc. An electrical signal can be formed, for example, without voltage supply by a piezoelectric sensor if, for example, a pressure situation in the body region is monitored. The electrical signal can then be analyzed in a conventional manner. In general, the output signals of the sensors can be transmitted to an analysis stage inside the contact arrangement or also to an external analysis arrangement. This transmission can take place via a line or also wirelessly via close-range communication (for example, according to the Bluetooth standard).

The invention claimed is:

1. A planar flexible contact arrangement, comprising:
a contact surface configured for contact on a body region of a living being;
at least one electrode arranged above the contact surface;
a dielectric material embedding the at least one electrode, wherein the at least one electrode has a supply line for an AC high voltage to form a dielectric barrier plasma;
at least one sensor for ascertaining at least one parameter of the body region, wherein the at least one sensor is connected to an electric voltage separate from the supply line for the AC high voltage; and one or more of
a) a terminal arrangement for a supply voltage for the at least one sensor; and
b) a battery arrangement for a supply voltage for the at least one sensor.

2. The contact arrangement as claimed in claim 1 wherein the at least one sensor is configured for measuring an oxygen saturation in the body region.

3. The contact arrangement as claimed in claim 1 wherein the at least one sensor is configured for measuring a local temperature in the body region.

4. The contact arrangement as claimed in claim 1 wherein the at least one is configured for detecting a color change in the body region.

5. The contact arrangement as claimed in claim 1 wherein the at least one sensor is configured for measuring the pH value in the body region.

6. The contact arrangement as claimed in claim 1 wherein the at least one sensor comprises multiple sensors for detecting a same measurement parameter, and are arrangeable at different points of the body region.

7. The contact arrangement as claimed in claim 1 wherein the at least one sensor comprises multiple sensors which differ from one another and detect different measurement parameters.

8. The contact arrangement as claimed in claim 1, further comprising:
a high-voltage step for generating AC high voltage for the at least one electrode from an output voltage of a battery arrangement of the contact arrangement.

9. A method of treating a body region of a living being, comprising:
contacting the body region of the living being with the planar flexible contact arrangement of claim 1;
sensing at least one parameter of the body regions of the living being with the at least one sensor of the planar flexible contact arrangement; and
forming the dielectric barrier plasma with the planar flexible contact arrangement after the at least one parameter is sensed by the at least one sensor.

* * * * *